US006942626B2

(12) United States Patent
Salisbury et al.

(10) Patent No.: US 6,942,626 B2
(45) Date of Patent: Sep. 13, 2005

(54) APPARATUS AND METHOD FOR IDENTIFYING SLEEP DISORDERED BREATHING

(75) Inventors: John I. Salisbury, Chepachet, RI (US); Tracey A. Dodenhoff, North Attleboro, MA (US)

(73) Assignee: Predictive Technologies, Inc., North Attleboro, MA (US)

( * ) Notice: Subject to any disclaimer, the term of this patent is extended or adjusted under 35 U.S.C. 154(b) by 0 days.

(21) Appl. No.: 10/897,304

(22) Filed: Jul. 22, 2004

(65) Prior Publication Data

US 2005/0020930 A1 Jan. 27, 2005

Related U.S. Application Data

(60) Provisional application No. 60/489,774, filed on Jul. 24, 2003.

(51) Int. Cl.[7] .................................................. A61B 5/08
(52) U.S. Cl. ....................... 600/538; 600/529; 600/509; 600/300
(58) Field of Search ................................. 600/300, 301, 600/508, 509, 529–543; 607/2, 6, 17, 18; 702/189–191, 193–197

(56) References Cited

U.S. PATENT DOCUMENTS

| | | | |
|---|---|---|---|
| 5,769,084 A | | 6/1998 | Katz et al. |
| 6,381,559 B1 | * | 4/2002 | Huang ........................ 702/194 |
| 6,580,944 B1 | * | 6/2003 | Katz et al. .................. 600/513 |
| 6,738,734 B1 | | 5/2004 | Huang |
| 2003/0033094 A1 | | 2/2003 | Huang |

OTHER PUBLICATIONS

Huang et al. "Use of Intrinsic Modes in Biology: Examples of indicial response of pulmonary blood pressure to +– step hypoxia", Proc. Natl. Acad. Sci. USA vol. 95, pp. 12766–12771, Oct. 1998.*

Huang et al. "Engineering analysis of biological variables: An example of blood pressure over 1 day", Proc. Natl. Acad. Sci. USA vol. 95, pp. 4816–4821, Apr. 1998.*

Huang, Norden E. et al, The Empirical Mode Decomposition And The Hilbert Spectrum For Nonlinear And Non–Stationary Time Series Analysis, Proc. Roy Soc. London, pp. 903–955, © 1998.

Huang, Norden E. et al, (Abstract)—A New View of Non-linear Waves; The Hilbert Spectrum, Annual Review of Fluid Mechanics, Jan. 1999.

Katz Richard A., Chaotic Circuits for Communication, International Society for Optical Engineering, vol. 2612, Oct. 1995.

Analyze Nonlinear Non–Stationary signals with Hilbert Huang Transform, Web site—http://techtransfer.gsfc.nasa.gov/hht/hht.htm.

Superior Algorithms for Analyzing Nonlinear Non–Stationary Data Web site—http://techtransfer.gsfc.nasa.gov/hht/attachments/hht–brochure–med.ptf.

* cited by examiner

*Primary Examiner*—Robert Nasser
*Assistant Examiner*—Patricia Mallari
(74) *Attorney, Agent, or Firm*—Fleit Kain Gibbons Gutman Bongini Bianco; Paul D. Bianco; Martin Fleit

(57) ABSTRACT

An apparatus and method for identifying sleep disordered breathing while the patient is awake. The device includes collection of raw data which is normalized, then conditioned and transformed for comparison against a threshold, enabling identification of the presence of and severity of sleep disordered breathing. Step 1 is the collection of raw data and normalization. Step 2 is the conditioning of the data (using Empirical Mode Decomposition or similar technique). Step 3 is the selection of several components in the conditioned data. Step 4 is the performing of a Hilbert transform on the conditioned data. Step 5 is selecting a constant frequency. Step 6 is charting output against a threshold. Step 7 is identifying the patient's condition based on an array of amplitudes and the threshold.

20 Claims, 1 Drawing Sheet

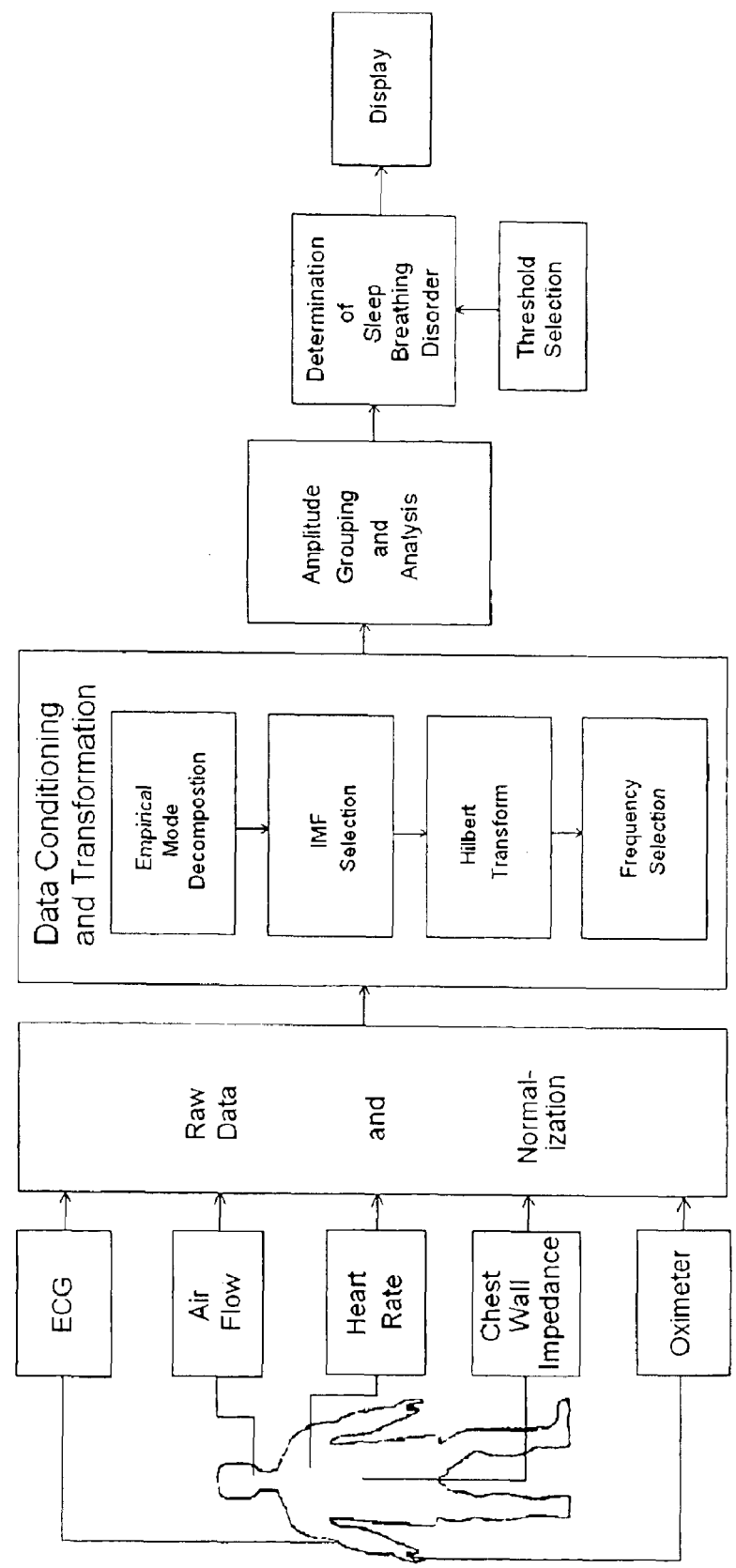

APPARATUS AND METHOD FOR IDENTIFYING SLEEP DISORDERED BREATHING

CROSS-REFERENCE TO RELATED APPLICATION

The present application claims priority to U.S. provisional application Ser. No. 60/489,774 filed Jul. 24, 2003. The provisional application is hereby incorporated by reference.

FIELD OF THE INVENTION

The present invention relates generally to sleep breathing diagnostic, and more specifically, it relates to an apparatus and method for identifying sleep disordered breathing for the rapid identification of sleep disordered breathing even when the patient is awake.

BACKGROUND OF THE INVENTION

It can be appreciated that sleep breathing diagnostic has been in use for years. Typically, sleep breathing diagnostic is comprised of polysomnography equipment for overnight sleep studies.

While these devices may be suitable for the particular purpose to which they address, they are not as suitable for the rapid identification of sleep disordered breathing while the patient is awake. The main problem with conventional sleep breathing diagnostic is sleep studies require significant resources. Generally, they are conducted in special facilities. One patient is located in one room for the night and typically arrives about 8:00 pm and leaves about 6:00 am. At least two trained technicians generally are present for the duration of each test. The technicians attach various sensors to the head, chest, arms and legs and then monitor the various signals from different patients. The results as multichannel charts and observed events are then reviewed by one or two physicians of different specialties in order to determine the existence of sleep apnea or other respiratory dysfunction conditions. Given this requirement, conventional sleep studies require significant physical plant assets that are not available for other purposes. Another problem is the diagnosis is labor intensive, requiring copious training and preparation. Also, another problem is the process is uncomfortable and unpleasant for the patient, and often times, delivers inaccurate results due to the discomfort.

In these respects, the apparatus and method for identifying sleep disordered breathing according to the present invention substantially departs from the conventional concepts and designs of the prior art, and in so doing provides an apparatus primarily developed for the purpose of the rapid identification of sleep disordered breathing while the patient is awake.

SUMMARY OF THE INVENTION

In view of the foregoing disadvantages inherent in the known types of sleep breathing diagnostic now present in the prior art, the present invention provides a new apparatus and method for identifying sleep disordered breathing construction wherein the same can be utilized for the rapid identification of sleep disordered breathing while the patient is awake.

The general purpose of the present invention, which will be described subsequently in greater detail, is to provide a new apparatus and method for identifying sleep disordered breathing that has many of the advantages of the sleep breathing diagnostic mentioned heretofore and many novel features that result in a new apparatus and method for identifying sleep disordered breathing which is not anticipated, rendered obvious, suggested, or even implied by any of the prior art sleep breathing diagnostic, either alone or in any combination thereof.

To attain this, the present invention generally includes collection of raw data which is normalized, then conditioned and transformed for comparison against a threshold, enabling identification of the presence of and severity of sleep disordered breathing. Step 1 is the collection of raw data and normalization. Step 2 is the conditioning of the data (using Empirical Mode Decomposition or similar technique). Step 3 is the selection of several components in the conditioned data. Step 4 is the performing of a Hilbert Transform on the conditioned data to generate a three-dimensional array of time, amplitude, and frequency. Step 5 is selecting a critical frequency, f0, and extracting a two-dimensional array of amplitude and time. Step 6 is charting output against a threshold. Step 7 is identifying the patient's condition based on an array of amplitudes and the threshold.

There has thus been outlined, rather broadly, the more important features of the invention in order that the detailed description thereof may be better understood, and in order that the present contribution to the art may be better appreciated. There are additional features of the invention that will be described hereinafter. Also, other features that relate to the invention and can be used with the invention (such as ways in which the raw data can be collected and normalized) have been set forth in U.S. Pat. Nos. 6,580,944 B1 and 5,769,084, the contents of which are incorporated by reference herein.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

A primary object of the present invention is to provide an apparatus and method for identifying sleep disordered breathing that will overcome the shortcomings of the prior art devices.

An object of the present invention is to provide an apparatus and method for identifying sleep disordered breathing that identifies the presence of sleep disordered breathing in a patient while the patient is awake.

Another object is to provide an apparatus and method for identifying sleep disordered breathing that identifies the presence of sleep disordered breathing using one or more cardio-respiratory input.

Another object is to provide an apparatus and method for identifying sleep disordered breathing that increases patient comfort.

Another object is to provide an apparatus and method for identifying sleep disordered breathing that reduces the need for multiple tests that result from patient discomfort.

Another object is to provide an apparatus and method for identifying sleep disordered breathing that creates on ongoing benchmark for tracking patient health.

Another object is to provide an apparatus and method for identifying sleep disordered breathing that rapidly diagnoses and/or screens sleep disordered breathing.

Another object is to provide an apparatus and method for identifying sleep disordered breathing that reduces the cost of diagnosing sleep disordered breathing.

Other objects and advantages of the present invention will become obvious to the reader, and it is intended that these objects and advantages are within the scope of the present invention.

To the accomplishment of the above and related objects, this invention may be embodied in the form illustrated in the accompanying drawing, attention being called to the fact, however, that the drawing is illustrative only, and that changes may be made in the specific construction illustrated.

BRIEF DESCRIPTION OF THE DRAWINGS

Various other objects, features and attendant advantages of the present invention will become fully appreciated as the same becomes better understood when considered in conjunction with the accompanying drawing, in which like reference characters designate the same or similar parts throughout the several views, and wherein:

FIG. 1 is a schematic view of the present invention showing the components.

DETAILED DESCRIPTION OF THE INVENTION

Turning now descriptively to the drawing, FIG. 1 illustrates an apparatus and method for identifying sleep disordered breathing, which comprises collection of raw data which is normalized, then conditioned and transformed for comparison against a threshold, enabling identification of the presence of and severity of sleep disordered breathing. Step 1 is the collection of raw data and normalization. Step 2 is the conditioning of said data using Empirical Mode Decomposition (EMD) or a similar technique. Step 3 is the selection of several components of the conditioned data. This step involves selecting a number of intrinsic model functions (IMF) generated by the EMD. Step 4 is the performing of a Hilbert transform on the conditioned data. The Hilbert transform is performed on the selected IMFs, thereby generating a three-dimensional array of time, amplitude, and frequency. Step 5 is selecting a critical frequency, f0, and extracting a two-dimensional array of amplitude and time. Step 6 is charting output against a threshold. Step 7 is identifying the patient's condition based on an array of amplitudes and the threshold.

Step 1 is the collection of raw data and normalization. The apparatus embodying this invention includes one or more monitors, each of which monitors and records at least one cardio-respiratory function of a patient over time. The cardio-respiratory function may include, but is not limited to, an electrocardiogram (ECG), air flow, heart rate, chest wall impedance, and oxygen saturation of blood (oximeter). The data is normalized upon collection. It has been found that a measurement of a single cardio-respiratory function can provide sufficient data for making a diagnosis. In a preferred embodiment, air flow data is collected. In some situations it may be desirable to use a measurement of another cardio-respiratory function exclusively of the air flow measurement or as a complement to the air flow measurement. The results from the complementary measurement could then be used to corroborate the signals from the air flow monitor.

There are numerous methods of acquiring the raw data. One of the monitors could be an air flow monitor that monitors oral nasal airflow. Any of a number of different flow and pressure transducer-based monitors can be used to provide a signal that accurately models the air flow from the patient. The output of the air flow monitor may generate a strip chart, and the function of the selector could be provided by apparatus that automatically or with manual intervention provides an input to a digital-to-analog converter or otherwise enables the signal to be submitted into the processor in an analog form. Alternatively and preferably, the analog signals from the air flow monitor could be digitized immediately for storage in a local memory. Standard normalization methods are used prior to conditioning.

Step 2 is the conditioning of the data using Empirical Mode Decomposition or a similar technique. The normalized data is conditioned, or decomposed using the Empirical Mode Decomposition (EMD). Further details concerning the EMD are found in the following references, the contents of which are hereby incorporated herein by reference: Huang, N. E., Z. Shen, S. R. Long, M. C. Wu, H-H. Shih, Q. Zheng, N-C. Yen, C-C. Tung and H-H. Liu, The empirical mode decomposition and the Hilbert spectrum for nonlinear and non-stationary time series analysis. Proc. Roy. Soc. London Ser. A, 454, 903–995, 1998. Huang, N. E., Z. Shen, S. R. Long, A new view of nonlinear water waves: the Hilbert spectrum, Annual Review of Fluid Mechanics, 31, 417–457, 1999.

The EMD generates a number of intrinsic model functions (IMF). For example, with approximately 5 minutes of normalized data, 10 to 14 IMFs can be generated. The first is the smallest scale or highest frequency where the last is for the largest scale or lowest frequency. There are a number of methods for conditioning the data, making it suitable for use with the Hilbert transform. Any of these methods could be used as an alternative to the EMD.

Step 3 is the selection of IMFs from the conditioned data. One or more IMFs may be selected. In an exemplary embodiment, two IMFs are selected from the resulting EMD. These IMFs are used for analysis with the Hilbert transform. Selection of the IMFs can be achieved through a number of methods, including arbitrary selection or programmed selection. Preferably, the selected IMFs are chosen based on the frequencies. In one exemplary embodiment, two or three IMFs having the highest frequencies are selected. In another embodiment, two or three IMFs having the next highest frequencies are selected.

Step 4 is the performance of a Hilbert transform on the conditioned data. A Hilbert transform is performed on the selected IMF's, thereby generating a three-dimensional array consisting of frequency, time, and amplitude. It should be understood that a Hilbert transform or any other non-linear, non-stationary mathematical method can be used.

Step 5 is selecting a frequency, f0. A two-dimensional array of amplitude and time is generated for the constant, f0. The selected frequency may range from about 0.1 Hz to about 3 Hz. Preferably, a frequency of 1.5 Hz may be used. However, the frequency can be changed to suit a particular application. The frequency setting will vary with the desired output, and may be changed or adjusted to calibrate the desired output.

Step 6 is charting output against a threshold. The output is a two-dimensional array of time and amplitude. This output can vary depending on the scale and axis selected. The threshold may be selected arbitrarily, by computer program, and/or based on control data. The threshold may be a cumulative number of amplitude data points within a selected range of amplitude levels.

Step 7 is identifying the patient's condition based on an array of amplitudes and the threshold. A histogram or other graphic representation is now generated using the two-dimensional array which results in an array with the number of amplitudes within a predetermined range of magnitudes arranged in bins. The number of bins may be determined through a variety of methods, including arbitrary selection, programmed selection, and/or based on control data. In an exemplary embodiment, the number of amplitude data points within the first 20 bins are counted, resulting in the cumulative number that indicates whether the patient has sleep disordered breathing or not. In another exemplary embodiment, the bins selected for counting contain the lowest amplitudes of the two-dimensional amplitude-time array.

The cumulative number is compared with the threshold. The threshold may be selected arbitrarily, by computer program, and/or based on control data. In an exemplary embodiment, the threshold is 300. Therefore, any cumulative number greater than the threshold of 300 indicates that the patient does not have sleep disordered breathing. Any number of methods of plotting the output could provide useful, for example, a bar chart that plots each data point. It is contemplated that the threshold as well as the number of bins counted may depend on the patient population characteristics.

This method and apparatus provides essentially the same information in a short test while the patient is awake as when the patient is asleep for a long interval. Moreover, it has been found that the number of measurements that must be taken can be reduced. In this particular embodiment only nasal airflow was monitored, eliminating the myriad sensors utilized in conventional sleep studies. This further simplifies the diagnostic procedures. Consequently, the physical assets of a hospital that must be devoted to such a test can be significantly reduced for the test.

Moreover, even assuming an interval for allowing the patient to be interviewed, prepared and tested for up to one hour, it should be possible to run 8 or more tests during normal working hours in the same time that would be required to conduct one sleep study after normal business hours. As a result, the number of patients that can be screened at a given facility can be greatly increased over the number that can be screened using conventional sleep studies at a significantly lower cost. Any number of available conditioning systems can be utilized to generate the information generated by the EMD. This invention has been disclosed in terms of certain embodiments. It will be apparent that many modifications can be made to the disclosed apparatus without departing from the invention. For example, temperature measurements of air flow could be modified to pressure measurements of air flow to yield similar information.

As to a further discussion of the manner of usage and operation of the present invention, the same should be apparent from the above description. Accordingly, no further discussion relating to the manner of usage and operation will be provided.

In order to describe the operation and utility of the present invention, the method is demonstrated to physiologic recordings from a blind trial of 29 patients in which data were collected at a major hospital (in Baltimore, Md.) and in which the patients were also subjected to a full nighttime conventional (8–10 hours) polysomography in which Apnea Hypopnea Index (AHI) scores were made available only to the hospital physicians and clinicians. On a separate occasion, the same patients were re-tested during the daytime in a short time interval using the methods and apparatus of the present invention. For the daytime test, the patient condition (degree of apnea) was not revealed to the examiners of the nonlinear method.

The results of the trial showed that for patients whose baseline polysomnography scores were in the range of AHI indices of 5 and above, where an index of 5 or greater defines the presence of a sleep disorder (i.e., apnea), the present invention was successful 86.2% of the time (i.e., 25 of 29 correct classifications of patients). For an AHI index of less than 5, considered as the normal range, there were 2 false positive classifications. For an AHI index of more than 5, considered sick, there were two false negative classifications.

Note that the scoring of the AHI and diagnosis of the patient's respiratory condition from nighttime polysomnography measurements alone remains an imprecise science, and different demarcations of the AHI index denoting a patient who is apnea afflicted (e.g., AHI index greater than 4, greater than 5, or greater than 12, as examples) remains a subjective call on the part of the attending physician or clinician. On the other hand, the method of the present invention is fully automated and computerized, and is completely defined in quantifiable terms in which human subjectivity is removed from the scoring process. A unique feature of the method is that various thresholds invoked during the data processing are determined from the data itself, rather than by arbitrarily imposing thresholds, as is often the case for a large variety of signal detection algorithms.

While the instant invention has been shown and described herein in what are conceived to be the most practical and preferred embodiments, it is recognized that departures, modifications, adaptations and variations may be made therefrom within and without departing from the scope of the invention, which is therefore not to be limited to the details disclosed herein, but also embraces any and all equivalent apparatus and articles.

What is claimed is:

1. A method for identifying sleep disordered breathing of a patient, the method comprising:
    collecting data of at least one cardio-respiratory function of the patient over time;
    generating a plurality of intrinsic mode functions from the data;
    generating an array of frequencies, times, and amplitudes based on at least one intrinsic mode function;
    generating an array of times and amplitudes based on a selected frequency; and
    identifying sleep disordered breathing of the patient from the generated amplitudes.

2. The method of claim 1 further including grouping the amplitudes from the array of times and amplitudes into a plurality of bins, each bin including amplitudes being within a predetermined range of magnitudes.

3. The method of claim 2 further including determining a cumulative number of amplitudes within a selected number of bins.

4. The method of claim 3 wherein the selected bins include amplitudes having the lowest magnitudes.

5. The method of claim 4 wherein identifying sleep disordered breathing includes comparing the cumulative number of amplitudes with a threshold.

6. The method of claim 5 wherein if the cumulative number of amplitudes is less than the threshold then the patient has sleep disordered breathing.

7. The method of claim 2 wherein the data includes respiratory airflow data.

8. The method of claim 2 wherein the data is collected while the patient is awake.

9. The method of claim 2 wherein the plurality of intrinsic mode functions is generated using Empirical Mode Decomposition.

10. The method of claim 2 wherein two intrinsic mode functions are selected.

11. The method of claim 2 wherein the array of frequencies, times, and amplitudes is generated from a Hilbert transform.

12. The method of claim 2 wherein a graphical representation represents the plurality of bins.

13. The method of claim 12 wherein the graphical representation is a histogram.

14. The method of claim 2 wherein the collected data is normalized.

15. A method for identifying sleep disordered breathing of a patient, the method comprising:

collecting air flow data of the patient over time while the patient is awake;

normalizing the air flow data;

generating a plurality of intrinsic mode functions from the data using Empirical Mode Decomposition;

selecting at least two intrinsic mode functions;

performing a Hilbert transform on the two intrinsic mode functions to generate an array of frequencies, times, and amplitudes;

generating an array of times and amplitudes based on a selected frequency;

grouping the amplitudes from the array of times and amplitudes into a plurality of bins, each bin including amplitudes being within a predetermined range of magnitudes;

determining a cumulative number of amplitudes within a selected number of bins, the selected bins including amplitudes having the lowest magnitudes; and diagnosing the patient with sleep disordered breathing if the cumulative number of amplitudes is less than a threshold.

16. The method of claim 15 wherein the selected frequency is 1.5 Hz.

17. The method of claim 15 wherein the selected number of bins is 20.

18. The method of claim 15 wherein the threshold is 300.

19. An apparatus for identifying sleep disordered breathing of a patient comprising:

collecting means for collecting data of at least one cardio-respiratory function of the patient over time;

first means for generating a plurality of intrinsic mode functions from the data;

second means for generating an array of frequencies, times, and amplitudes based on at least one intrinsic mode function;

third means for generating an array of times and amplitudes based on a selected frequency; and identifying means for identifying sleep disordered breathing of the patient from the generated amplitudes.

20. The apparatus of claim 19 further including grouping means for grouping the amplitudes from the array of times and amplitudes into a plurality of bins, each bin including amplitudes being within a predetermined range of magnitudes.

* * * * *